US010137165B2

(12) United States Patent
Gronski et al.

(10) Patent No.: US 10,137,165 B2
(45) Date of Patent: Nov. 27, 2018

(54) FACTOR H FOR THE TREATMENT OF CHRONIC NEPHROPATHIES AND PRODUCTION THEREOF

(75) Inventors: Peter Gronski, Marburg (DE); Christoph Licht, Toronto (CA); Bernd Hoppe, Bonn (DE); Peter Zipfel, Jena (DE); Christine Skerka, Jena (DE)

(73) Assignee: CSL BEHRING GMBH, Marburg (DE)

( * ) Notice: Subject to any disclaimer, the term of this patent is extended or adjusted under 35 U.S.C. 154(b) by 1183 days.

(21) Appl. No.: 12/916,807

(22) Filed: Nov. 1, 2010

(65) Prior Publication Data

US 2011/0046062 A1 Feb. 24, 2011

Related U.S. Application Data

(63) Continuation of application No. 11/992,194, filed as application No. PCT/EP2006/005631 on Jun. 13, 2006, now abandoned.

(30) Foreign Application Priority Data

Sep. 19, 2005 (EP) .................................. 05020409

(51) Int. Cl.
| | |
|---|---|
| A61K 38/17 | (2006.01) |
| A61K 38/04 | (2006.01) |
| C07K 16/18 | (2006.01) |
| C07K 14/435 | (2006.01) |
| A61K 39/395 | (2006.01) |

(52) U.S. Cl.
CPC .......... *A61K 38/04* (2013.01); *A61K 39/3955* (2013.01); *C07K 14/435* (2013.01); *C07K 16/18* (2013.01)

(58) Field of Classification Search
None
See application file for complete search history.

(56) References Cited

U.S. PATENT DOCUMENTS 4,883,784 A 11/1989 Kaneko

FOREIGN PATENT DOCUMENTS

| EP | 0 222 611 A2 | 5/1987 |
| EP | 0 222 611 B1 | 3/1991 |

OTHER PUBLICATIONS

Alsaad et al, Journal of Clinical Pathology, 2007; vol. 60, pp. 18-26.*
Silva et al, Toxicologic Pathology, 2004, vol. 32, Suppl. 2, pp. 71-84.*
Alchi et al, Pediatric Nephrology, 2010, vol. 25, pp. 1409-1418.*
Goodship et al, Kidney International, 2006, vol. 70, pp. 12-13.*
Fakhouri et al, Kidney International, 2010, vol. 78, (3), pp. 279-286.*
Prodromidi et al, Stem Cells, 2006, vol. 24, pp. 2448-2455.*
Atypical hemolytic uremic syndrome, National Library of Medicine, 2011.*
Dense Deposit Disease, National Library of Medicine, 2011.*
Makou et al, Biochemistry, 2013; vol. 52, pp. 3949-3962.*
Van der Maten et al, PLOS One, 2016, vol. 10, pp. 1-11.*
Appel, G.B., et al., "Membranoproliferative glomerulonephritis type II (dense deposit disease): An update," J. Am. Soc. Nephrol, 16, pp. 1392-1403, 2005.
Ault, B.H., "Factor H and the Pathogenesis of Renal Diseases," Pediatr Nephrol, 14, pp. 1045-1053, 2000.
Bettini, et al., Book review of "Handbook of Pharmaceutical Excipients, Third Edition, Arthur H. Kibbe (ed.), Pharmaceutical Press, London, 2000, 665 pp.," Book reviews / Journal of Controlled Release 71, pp. 352-353 (2001).
Brenner, B.M., et al., "The Role of Hemodynamically Mediated Glomerular Injury in the Pathogenesis of Progressive Glomerular Sclerosis in Aging, Renal Ablation, and Intrinsic Renal Disease," The New England Journal of Medicine, 307, pp. 652-659, 1982.
Crossley, L.G. et al., "Purification of the Human Complement Control Protein C3b Inactivator," Biochem J, 191, pp. 173-182, 1980.
Endo, M., et al., "Glomerular deposition and urinary excretion of complement Factor H in idiopathic membranous nephropathy," Nephron Clin. Pract., 97, pp. c147-c153, 2004.
Estaller, C., et al., "Human complement factor H: Two factor H proteins are derived from alternatively spliced transcripts," European Journal of Immunology, 21(3), pp. 799-802, 1991.
European Search Report for Application No. 05020409.8-2107, dated Apr. 7, 2006.
Haines, J.L., et al., "Complement Factor H Variant Increases the Risk of Age-Related Macular Degeneration," Sciencexpress, 10.1126/science.1110359, pp. 1-6, 2005.
Høgåsen, K., et al., "Hereditary Porcine Membranoproliferative Glomerulonephritis Type II is Caused by Factor H Deficiency," J. Clin. Invest, 95, pp. 1054-1061, 1995.
Hsu, S. I-Hong, et al., "Chronic progression of tubuloinsterstitial damage in proteinuric renal disease is mediated by complement activation: A therapeutic role for complement inhibitors?" J. Am. Soc. Nephrol., 14, pp. S186-S191, 2003.
International Search Report and Written Opinion for PCT/EP2006/005631, dated Sep. 27, 2006.
Jansen, J.H., et al., "In situ complement activation in porcine membranoproliferative glomerulonephritis type II," Kidney Int'l., 53, pp. 331-349, 1998.
Jerums, G., et al., "Why is Proteinuria such an Important Risk Factor for Progression in Clinical Trials?", Kidney International, 52, Suppl. 63, pp. 87-92, 1997.

(Continued)

Primary Examiner — Bridget E Bunner
Assistant Examiner — Fozia Hamud
(74) Attorney, Agent, or Firm — Finnegan, Henderson, Farabow, Garrett & Dunner, L.L.P.

(57) ABSTRACT

The invention relates to the use of Factor H for the manufacture of a medicament to treat both chronic nephropathies which are not causally associated with proteinuria and chronic nephropathies which are causally associated with proteinuria. The invention also relates to large scale purification methods for Factor H.

14 Claims, No Drawings

(56) References Cited

OTHER PUBLICATIONS

Józsi, M., et al., "Attachment of the Soluble Complement Regulator Factor H to Cell and Tissue Surfaces: Relevance for Pathology," Histol Histopathol, 19, pp. 251-258, 2004.

Klein, R.J., et al., "Complement Factor H Polymorphism in Age-Related Macular Degeneration," Sciencexpress, 10.1126/science.1109557, pp. 1-8, 2005.

Kolbjorn, H., et al., "Porcine membranoproliferative glomerulonephritis (MPGN) type II is prevented and reversed by factor H substitution therapy," Mol. Immunol., 36:(4-5), p. 304, Abstract 104, 1999.

Kolbjorn, H., et al., "Procine membranoproliferative glomerulonephritis (MPGN) type II is reversed by factor H substitution therapy," J. Am. Soc. Nephrol., 9, pp. 474A-475A, Abstract A2206-T885PS, 1997.

Kriz, W., et al., "Pathways to nephron loss starting from glomerular diseases—Insights from animal models," Kidney Int'l., 67, pp. 404-419, 2005.

Lee, G., Book review of "Pharmaceutical Formulation Development of Peptides and Proteins, Sven Frokjaer, Lars Hovgaard, Taylor & Francis, Andover, UK, 2000, 238 pp.," Book reviews / European Journal of Pharmaceutics and Biopharmaceutics 50, p. 329 (2000).

Levy, Y., et al., "Partial Lipodystrophy, Mesangiocapillary Glomerulonephritis, and Complement Dysregulation," Immunologic Research, 18, pp. 55-60, 1998.

Licht, C., et al., "Deletion of Lys224 in Regulatory Domain 4 of Factor H Reveals a Novel Pathomechanism for Dense Deposit Disease (MPGN II)," Kidney International, 70, pp. 42-50, 2006.

Licht, C., et al., "Successful plasma therapy for atypical hemolytic uremic syndrome caused by Factor H deficiency owing to a novel mutation in the complement cofactor protein domain 15," Am. J. Kidney Dis., 45(2), pp. 415-421, 2005.

Mhatre, A., et al., "Isolation of bovine complement Factor H," Vet. Immunol. Immunopathol., 14, pp. 357-375, 1987.

Moure, F., et al., "Coupling process for plasma protein fractionation using ethanol precipitation and ion exchange chromatography," Meat Sci., 64, pp. 391-398, 2003.

Nagasawa, S., et al., "Purification and Characterization of a Macromolecular Weight Cofactor for C3b-Inactivator, C4bC3bINA-Cofactor, of Human Plasma," Molecular Immunology, 17, pp. 1365-1372, 1980.

Rastegar, A., et al., "The clinical spectrum of tubulointerstitial nephritis," Kidney Int'l., 54, pp. 313-327, 1998.

Ripoche, J., et al., "Isolation of Two Molecular Populations of Human Complement Factor H by Hydrophobic Affinity Chromatography," Biochem J, 221, pp. 89-96, 1984.

Rother, K., et al., "The Complement System," Springer Verlag, $2^{nd}$ rev ed., pp. 34-37, 1997.

Schultze, H.E., et al, "Molecular Biology of Human Proteins," Elsevier Publishing Company, vol. 1, pp. 236-317, 1966.

Schwertz, R., et al., "Outcome of Idiopathic Membranoproliferative Glomerulonephritis in Children," Acta Paediatr, 85, pp. 308-312, 1996.

Tang, S., et al., "Role of complement in tubulointerstitial injury from proteinuria," Kidney Blood Press Res., 25, pp. 120-126, 2002.

Thurman, J.M., et al., "Acute tubular necrosis is characterized by activation of the alternative pathway of complement," Kidney Int'l., 67, pp. 524-530, 2005.

Notice of Preliminary Rejection, issued in corresponding Korean Patent Application No. 10-2008-7006719, dated May 16, 2013.

Sánchez-Corral, Pilar, et al., "Structural And Functional Characterization Of Factor H Mutations Associated With Atypical Hemolytic Uremic Syndrome," Am. J. Hum. Genet., vol. 71, pp. 1285-1295 (2002).

Office Action, dated Mar. 17, 2014, in Canadian Patent Application No. 2,627,264 (3 pages).

Hogasen, K. et al., "Porcine membranoproliferative glomerulonephritis (MPGN) Type II is prevented and reversed by factor H substitution therapy," Molecular Immunology (Abstract 104), 36(4-5), p. 305, Mar. 3, 1999 (1 page).

Hogasen, K. et al., "Porcine membranoproliferative glomerulonephritis (MPGN) type II is reversed by factor H substitution therapy," Journal of the American Society of Nephrology (Abstract A2206), 9(Program and Abstract Issue), pp. 474A-475A, Sep. 9, 1997 (4 pages).

Jozsi et. al., "Factor H and Atypical Hemolytic Uremic Syndrome: Mutations in the C-Terminus Cause Structural Changes and Defective Recognition Functions," J. of Am. Society of Nephrology, vol. 17, pp. 170-177, (2006).

Loirat, C. et al., "Plasmatherapy in Atypical Hemolytic Uremic Syndrome," Thieme Medical Publishers, Inc., Nov. 6, 2010, pp. 673-681, vol. 36, USA (9 pages).

Nester, C. et al., "Atypical Hemolytic uremic syndrome: what is it, how is it diagnosed, and how is it treated?," American Society of Hematology, 2012, pp. 617-625 (9 pages).

\* cited by examiner

FACTOR H FOR THE TREATMENT OF CHRONIC NEPHROPATHIES AND PRODUCTION THEREOF

CROSS-REFERENCE TO RELATED APPLICATIONS

This is a continuation of application Ser. No. 11/992,194, now abandoned which is the United States national stage of PCT/EP2006, 005631, filed Jun. 13, 2006, which claims priority to European Application No. 05 020409.8, filed Sep. 19, 2005, all of which are incorporated herein by reference.

BACKGROUND OF THE INVENTION

The invention relates to the use of Factor H for the manufacture of a medicament to treat both chronic nephropathies which are not causally associated with proteinuria and chronic nephropathies which are causally associated with proteinuria. The invention also relates to large scale purification methods for Factor H.

The complement system comprising more than 40 different proteins directly or indirectly mediates attack and elimination of microbes, foreign particles and altered self cells via three different pathways of activation (alternative, lectin and classical pathway; Rother K et al. (Eds) The Complement System. $2^{nd}$ revised edition, 1998; Springer Verlag). This process is highly restricted in terms of time and space and can discriminate between self (host cells) and foreign (e.g., microbes).

Some human diseases are obviously accompanied by an activation of these cascade-like activation pathways which is reflected by the occurrence of elevated levels of typical activation markers comprising the range from early to late components of the complement system, including inhibitor-protease complexes. Moreover, the sometimes observed cellular damage is taken as indicator of at least a local derailment of the complement system which usually is under tight control. From a quantitative point of view, proteolytic cleavage of C3 by specific C3 convertases plays a major role for complement activation. These convertases generate forms of C3b, which represent a potential component of new C3 convertase molecules, thereby stimulating the cascade.

The protection of self-cells and tissue is mediated by specific regulators or inhibitors, existing in the fluid-phase and/or in membrane-bound forms. These regulators include complement receptor 1 (CR1 or CD35: binds C3b and C4b, disassembles C3 convertases and permits C3b/C4b degradation by factor I), decay accelerating factor (DAF or CD55: binds C3b and disassembles C3/C5 convertase) and membrane co-factor protein (MCP or CD46: binds C3b and C4b to permit their degradation by factor I), which all are exclusively membrane-anchored proteins.

In addition to the membrane-anchored control proteins, the attachment of the soluble complement regulator Factor H (single-chain glycoprotein composed of 20 short consensus repeats, SCRs; 155 kDa; ~9.3% carbohydrate) to the polyanionic surface of self cells represents a potent component for protection of the cell surface by increasing the inhibitory potential (JOzsi M et al.; Histol Histopathol 2004; 19:251-8). This protection is mainly achieved by efficiently reducing the lifetime of the alternative C3 convertase (C3bBb) by both binding to the covalently bound C3b and displacing Bb (decay acceleration), and catalysing the permanent inactivation of C3b via proteolytic cleavage by the serine proteinase Factor I (co-factor activity: generation of, e.g., iC3b, C3c; Rother K et al. ($2^{nd}$ revised edition) The Complement System. 1998, Springer Verlag; p. 28, 34-7). The activity of Factor H as co-factor for the protease factor I in the outer phase of the surface layer (approx. 20-140 nm) is facilitated by binding of Factor H to surface-located proteoglycans by means of the C-terminal SCR (JOzsi M et al.; Histol Histopathol 2004; 19:251-8). The protective potential of Factor H limits locally the progression of the complement cascade. This is of particular importance for cells which express a low number of the above mentioned membrane-anchored regulators, or for tissues which completely lack those endogenous control proteins, such as the kidney glomerular basement membrane (Hogasen K et al.; J Clin Invest 1995; 95:1054-61).

Patent EP 0 222 611 B1 comprises the use of Factor H in immune complex related diseases in which Factor H is only temporarily decreased, to downregulate complement activation, "Factor H and/or Factor I for use in the treatment of a vascular autoimmune disease", "Factor H and/or Factor I for use in the treatment of systemic lupus erythematosus, rheumatoid arthritis or glomerulonephritis", and "A process for preparing a pharmaceutical composition for use in the treatment of a vascular autoimmune disease comprising mixing Factor H and/or Factor I with a pharmaceutically acceptable carrier, diluent or adjuvant". However, the scope of this patent is unequivocally related to glomerulonephritis as an immune complex (IC)-mediated nephropathy with glomerular deposition/formation of ICs generated outside or inside the kidney (e.g., Goodpasture-syndrom). In EP 0 222 611 B1 no teaching is comprised on the treatment of antibody-independent chronic nephropathies like, e.g., tubulointerstitial fibrosis (TIF), which specifies the formation of fibrous tissue within the space between the tubuli (interstitium).

BRIEF SUMMARY OF THE INVENTION

One embodiment of the invention is the use of Factor H for the manufacture of a medicament to treat antibody independent chronic nephropathies, which are not causally linked to proteinuria.

A missing or significantly reduced function of Factor H, either due to missing or reduced protein levels of the functionally active molecule or due to respective gene mutation(s) in molecular regions which are important to mediate this function by binding of relevant ligands, has been demonstrated in diseases which finally harm kidney function like the atypical hemolytic uremic syndrome (aHUS) or the membranoproliferative glomerulonephritis type II (MPGN II). Since the glomerular membrane lacks endogenous regulators, continuous cleavage of C3 occurs at this site, resulting in deposition of complement activation products, presumably in formation of a C3 convertase-mediated damage of the glomerular basement membranes and of epithelial tubulus and endothelial cells, membrane thickening via deposition of extracellular matrix and/or components of the complement system (e.g., C3 split products) and of antibodies, and, consequently, in defective filtration (proteinuria).

MPGN II, also termed "dense deposit disease", is a rare disease which is characterized by complement containing dense deposits within the basement membrane of the glomerular capillary wall and followed by capillary wall thickening, mesangial cell proliferation and glomerular fibrosis (Ault B H; Pediatr Nephrol 2000; 14:1045-53).

Besides MPGN II, there are two more subtypes called MPGN I and MPGN III. All three subtypes are characterized by mesangial cell proliferation and increase in mesangial matrix combined with a thickening of the glomerular capillary walls (MPGN I: interposition of mesangial cells and matrix between basement membrane and endothelial cells resulting in the formation of a double structure; subendothelial electron dense deposits. MPGN III: subendothelial and subepithelial electron dense deposits). Deposits in all subtypes contain C3 and other complement factors. In some patients combination of MPGN with extrarenal manifestations like lipodystrophy and retina alterations can be found (Levy Y et. al.; Immunol Res 1998; 18:55-60).

MPGN mainly affects children and adults (median age at onset of disease: about 10 years). 50% of the patients present with nephrotic syndrome, the others with mild proteinuria, 20% with macrohematuria. 30% of the patients develop hypertension with onset of disease. Children with MPGN have an unfavourable late prognosis and develop end stage renal disease (ESRD) after about 8-16 years (MPGN I: 15.3 years; MPGN II: 8.7 years; MPGN III: 15.9 years; Schwertz R et al. Acta Paediatr 1996; 85:308-12).

Recent findings (Klein R J et al. Science 2005 Mar. 10; 10.1126/science.1109557; Haines J L et al. Science 2005 Mar. 10; 10.1126/science.1110359) indicate an association of an increased risk of age-related macular degeneration (AMD) and a Factor H variant (tyrosine-histidine change at amino acid 402 in the short consensus repeat number 7, SCR7). However, the causal relationship between a missing Factor H function (SCR7 contains binding sites for heparin, C-reactive protein and M-protein) and AMD has not yet been proven.

A possible therapy of Factor H associated aHUS- and MPGN II-patients is the administration of fresh frozen plasma, based on a weight-related treatment schedule (10-40 mL per kg of body weight biweekly). In this therapy the missing functional Factor H is restored to normal plasma levels. However, in cases where Factor H-protein is not reduced but is mutant such that it still binds to cellular membranes but has lost its ability of decay acceleration and/or co-factor activity to downregulate the complement system, mutant Factor H is competitively blocking the linkage of therapeutically added doses of normal Factor H to the membrane. Therefore, it is insufficient to restore physiological levels of functional Factor H on a molar bases, but doses raising the levels of Factor H above normal need to be administered in order to replace dysfunctional Factor H from the membrane.

DETAILED DESCRIPTION OF THE INVENTION

Factor H mutations can be divided as follows: (1) mutations which cause a block of Factor H secretion, e.g. from liver cells, resulting in the complete absence of Factor H in plasma, (2) mutations which result in a defect of Factor H function (a) in the regulatory domain of the protein (SCRs 1-4), (b) in the recognition domain of the protein (SCRs 19-20), or (c) in different parts of the protein affecting other functions e.g. heparin binding. While mutations in the recognition domain (2b) prevent Factor H protein from binding to surfaces, mutations in the regulatory domain (2a) results in a functionally defective Factor H but renders the protein capable to bind to surfaces.

Supplementation of Factor H via FFP infusion needs to achieve normal range plasma levels only in case (1) (=missing plasma Factor H) and (2b) (=mutations affecting Factor H binding). Supra-normal plasma Factor H levels, however, are required in cases (2a) and (2c) (=mutations affecting Factor H function while Factor H binding is unaffected) since endogenous inactive Factor H molecules compete with infused active Factor H molecules for surface binding sites.

One aspect of the current invention is therefore to treat antibody independent chronic nephropathies like aHUS or MPGN II with doses of functional Factor H which lead to supraphysiological plasma concentrations of the newly added Factor H as compared to natural concentrations of Factor H. Preferentially, the concentration of Factor H is increased by more than 10% above the treated patient's normal plasma levels. More preferentially, the concentration of Factor H is increased by more than 50%, even more preferentially by more than 100% or even more preferentially by more than 200% and most preferentially by more than 300% of the treated patient's normal plasma levels Another embodiment of the invention is the use of Factor H for the manufacture of a medicament to treat antibody independent chronic nephropathies, which are causally linked to proteinuria.

Prospective, randomized clinical trials have indicated that insufficient glomerular filtration of proteins is linked to proteinuria and is a major risk for the onset and progression of both interstitial fibrosis and progressive renal failure (Jerums G et al. Kidney Int Suppl 1997; 63:87-92). Little is known about the mechanisms responsible for the spread of tissue injury from the glomerular to the tubular compartment in diseases and how interstitial fibrosis is induced has not been addressed.

Activation of complement via the alternative pathway has been shown to be involved at the site of proximal tubular epithelial cells (reviewed in Tang S et al. Kidney Blood Press Res. 2002; 25:120-6), a mechanism known to be essentially antibody-independent.

Another more recent publication substantiates the antibody independent activation of the alternative pathway of complement as concomitant of acute tubular necrosis (Thurman J M et al. Kidney Int 2005; 67:524-30).

It has been demonstrated that protein overload in the absence of antibody deposition is associated with the activation of complement components on the apical membrane of proximal tubules. The proposed mechanism involved augmented intrarenal levels of ammonia (ammoniagenesis), a nucleophile which can activate C3, including the terminal complement cascade (reviewed in: I-Hong Hsu S, Couser W G. J Am Soc Nephrol 2003; 14:186-91). Various natural and artificial complement inhibitors, like soluble complement receptor 1, CR1, decay accelerating factor, DAF, and other molecules are discussed as potential therapeutic targets for pharmacologic intervention (see same review). However, the use of Factor H is not mentioned.

Thus the use of Factor H as a therapeutic for the protection of cellular membranes lacking endogenous membrane-anchored regulators is new and has not yet been investigated in in-vitro or in-vitro models. In general, patients with antibody independent chronic nephropathies which are causally associated with proteinuria, who benefit from Factor H have normal Factor H levels. The therapeutic effect is preferentially achieved by increasing the Factor H concentration to supraphysiological levels. The reason why this specific aspect has not been investigated so far may be due to the function of Factor H as a protease-associated co-factor, which is not consumed like a substrate.

One embodiment of the present invention is providing Factor H for the treatment of chronic nephropathies, which are causally associated with proteinuria, the generation of which is independent from antibody-mediated IC formation. Proteinuria can be primarily caused by alterations of structural proteins involved in the cellular mechanism of filtration. However, the subsequent presence of plasma proteins is thought to promote complement-mediated, IC-independent cellular damage which apparently happens in the absence of endogenous membrane regulators (e.g., CR1, DAF) despite normal levels of Factor H. The pathophysiological causes of proteinuria can be divided in the following major groups: (1) genetically determined disturbances of the structures which form the "glomerular filtration unit" like the glomerular basement membrane, the podocytes, or the slit diaphragm, (2) inflammatory processes, either directly caused by autoimmune processes or indirectly induced by microbes, (3) damage of the glomeruli caused by agents, or (4) as the final result of progressive tubulointerstitial injury finally resulting in the loss of function of the entire nephron. More specifically this invention relates to the use of Factor H to treat TIF on the level of the tubular epithelial cells where proteinuria induces the cascade of events (inflammation and fibrosis) which finally results in TIF. Doses of Factor H which lead to supraphysiological plasma concentrations of the newly added Factor H as compared to natural concentrations of Factor H are preferred embodiments of the present invention. Preferentially the concentration of Factor H is increased by more than 10% above the patient's individual normal plasma levels. More preferentially the concentration of Factor H is increased by more than 50%, even more preferentially by more than 100% or even more preferentially by more than 200% and most preferentially by more than 300% of the patients' individual normal plasma levels.

Factor H can be obtained from human plasma or serum or recombinantly. "Factor H" as used in the present invention comprises proteins that have the amino acid sequence of native human Factor H. It also comprises proteins with a slightly modified amino acid sequence, for instance, a modified N-terminal end including N-terminal amino acid deletions or additions so long as those proteins substantially retain the activity of Factor H. "Factor H" within the above definition also comprises natural allelic variations that may exist and occur from one individual to another. "Factor H" within the above definition further comprises of Factor H. Such variants differ in one or more amino acid residues from the wild type sequence. Examples of such differences may include truncation of the N- and/or C-terminus by one or more amino acid residues (e.g. 1 to 10 amino acid residues), or addition of one or more extra residues at the N- and/or C-terminus, e.g. addition of a methionine residue at the N-terminus, as well as conservative amino acid substitutions, i.e. substitutions performed within groups of amino acids with similar characteristics, e.g. (1) small amino acids, (2) acidic amino acids, (3) polar amino acids, (4) basic amino acids, (5) hydrophobic amino acids, (6) aromatic amino acids. Examples of such conservative substitutions are shown in the following table.

| (1) | Alanine | Glycine | | |
|---|---|---|---|---|
| (2) | Aspartic acid | Glutamic acid | | |
| (3a) | Asparagine | Glutamine | | |
| (3b) | Serine | Threonine | | |
| (4) | Arginine | Histidine | Lysine | |
| (5) | Isoleucine | Leucine | Methionine | Valine |
| (6) | Phenylalanine | Tyrosine | Tryptophane | |

"Functional Factor H" as used in this invention comprises Factor H molecules displaying activity either in solution and/or on cellular surfaces like decay acceleration of alternative C3 convertase and/or co-factor activity, catalyzing the permanent proteolysis of C3b by Factor I.

The term "recombinant" means, for example, that the variant has been produced in a host organism by genetic engineering techniques.

The host cells of the invention may be employed in a method of producing human Factor H. The method comprises:

a) culturing host cells of the invention under conditions such that human Factor H is expressed; and b) optionally recovering human Factor H from the host cells or from the culture medium.

Degree and location of glycosylation or other post-translation modifications may vary depending on the chosen host cells and the nature of the host cellular environment. When referring to specific amino acid sequences, posttranslational modifications of such sequences are encompassed in this application.

The production of recombinant proteins at high levels in suitable host cells, requires the assembly of the abovementioned modified cDNAs into efficient transcriptional units together with suitable regulatory elements in a recombinant expression vector, that can be propagated in various expression systems according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the cDNAs, the transcriptional unit should contain in its 3'-proximal part a DNA region encoding a transcriptional termination-polyadenylation sequence. Preferably, this sequence is derived from the Simian Virus 40 early transcriptional region, the rabbit beta-globin gene, or the human tissue plasminogen activator gene.

The cDNAs are then integrated into the genome of a suitable host cell line for expression of the Factor H. Preferably this cell line should be an animal cell-line of vertebrate origin in order to ensure correct folding, Gla-domain synthesis, disulfide bond formation, asparagine-linked glycosylation, O-linked glycosylation, and other post-translational modifications as well as secretion into the cultivation medium. Examples of other post-translational modifications are hydroxylation and proteolytic processing of the nascent polypeptide chain. Examples of cell lines that can be used are monkey COS-cells, mouse L-cells, mouse C127-cells, hamster BHK-21 cells, human embryonic kidney 293 cells, and preferentially hamster CHO-cells. Due to its complex post-translational modifications recombinant Factor H is preferably expressed in human cell lines.

The recombinant expression vector encoding the corresponding cDNAs can be introduced into an animal cell line in several different ways. For instance, recombinant expression vectors can be created from vectors based on different animal viruses. Examples of these are vectors based on baculovirus, vaccinia virus, adenovirus, and preferably bovine papilloma virus.

The transcription units encoding the corresponding DNAs can also be introduced into animal cells together with another recombinant gene which may function as a dominant selectable marker in these cells in order to facilitate the isolation of specific cell clones which have integrated the recombinant DNA into their genome. Examples of this type of dominant selectable marker genes are Tn5 amino glycoside phosphotransferase, conferring resistance to geneticin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated into the genome of the host cell, frequently resulting in a tight physical linkage between the different transcription units.

Other types of selectable marker genes, which can be used together with the cDNA of the desired protein, are based on various transcription units encoding dihydrofolate reductase (dhfr). After introduction of this type of gene into cells lacking endogenous dhfr-activity, preferentially CHO-cells (DUKX-B11, DG-44) it will enable these to grow in media lacking nucleosides. An example of such a medium is Ham's F12 without hypoxanthine, thymidin, and glycine. These dhfr-genes can be introduced together with the coagulation factor cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a bath culture or as a perfusion culture with continuous production of conditioned medium over extended periods of time. Thus, according to the present invention, the above cell lines are well suited for the development of an industrial process for the production of the desired recombinant proteins The recombinant protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

An example of such purification is the adsorption of the recombinant protein to a monoclonal antibody, which is immobilised on a solid support. After desorption, the protein can be further purified by a variety of chromatographic techniques based on the above properties.

It is preferred to purify Factor H of the present invention to ≥60% purity, more preferably ≥80% purity, and particularly preferred is a pharmaceutically pure state that is greater than 95% pure with respect to contaminating macromolecules, particularly other proteins and nucleic acids, and free of infectious and pyrogenic agents.

All of the potential purification procedures cited in EP 0 222 611 B1 are typical laboratory methodologies exclusively developed for purification of a single protein from human plasma or serum, disregarding the technology established in praxis by industry which is usually based on multicomponent-use with a focus on albumin, immunoglobulins and clotting factors. Industrial scale-procedures adapted to already established routine process routes are not yet existing.

Therefore, another objective of the present invention is to provide a production procedure for a plasma-derived version of human Factor H for therapeutic use suitable for large scale. Large scale with regard to the present invention means a production procedure based on at least 200 l plasma, preferentially at least 500 l, even more preferentially at least 2000 l human plasma. Regarding production, the claimed processes starting from human plasma shall be based on the subfractionation of typical industrial intermediates obtained by, e.g., the fractional precipitation by ethanol in the cold (reviewed in Schultze H E, Heremans J F; Molecular Biology of Human Proteins. Volume I: Nature and Metabolism of Extracellular Proteins 1966, Elsevier Publishing Company; p. 236-317). A preferred embodiment of such purification is the purification of functional Faktor H from side fractions of industrial scale plasma fractionation in such a way that established and licensed manufacturing processes of plasma products, which are under control of pharmaceutical regulatory authorities, like antithrombin (AT) or immunoglobulins are not affected. The supernatant of the 8% ethanol-precipitate (method of Cohn et al.; previous citation, p. 251) is one example of a source of Factor H, originating from industrial scale plasma fractionation. AT together with Factor H can be adsorbed from this supernatant by Heparin-based affinity chromatography and Factor H can be purified fractions of elution which do not contain AT. Precipitate III (method of Oncley et al.; previous citation, p. 253) or precipitate B (method of Kistler and Nitschmann; previous citation, p. 253) are other examples of such industrial sources for Factor H in case adsorption of AT is not routinely carried out. Starting from those side fractions, purification procedures known in the art can be used to purify Factor H. They may be based on precipitation with polyethylene glycol (Nagasawa S, Stroud R M; Mol Immunol 1980; 17:1365-72), affinity chromatography via immobilized heparin (citation as before), ion exchange chromatography (Crossley L G, Porter R R; Biochem J 1980; 191:173-82) and hydrophobic interaction chromatography (Ripoche J, Al Salihi A, Rousseaux J, Fontaine M; Biochem J 1984; 221, 89-96).

Factor H as described in this invention can be formulated into pharmaceutical preparations for therapeutic use. The purified protein may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", $3^{rd}$ edition, Kibbe et al., Pharmaceutical Press (2000)). In particular, the pharmaceutical composition comprising the polypeptide variant of the invention may be formulated in lyophilized or stable soluble form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known and can be used to administer the composition by any convenient route. Preferentially the compositions of the invention are administered systemically. For systemic use, Factor H of the invention is formulated for parenteral (e.g. intravenous, subcutaneous, intramuscular, intraperitoneal, intracerebral, intrapulmonar, intranasal or transdermal) or enteral (e.g., oral, vaginal or rectal) delivery according to conventional methods. The most preferential routes of administration are intravenous and subcutaneous administration. The formulations can be administered continuously by infusion or by bolus injection. Some formulations encompass slow release systems.

The Factor H of the present invention is administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

The pharmaceutical composition of the invention may be administered alone or in conjunction with other therapeutic agents. These agents may be incorporated as part of the same pharmaceutical.

Experimental Confirmation of Mode of Factor H Action

COL4α3 knock out mice, mimicking Alport syndrome (AS), express a defect α3 chain of collagen 4 causing a defect of the glomerular basement membrane. This results in glomerular proteinuria and progressive tubulointerstitial fibrosis beginning 4.5 weeks postpartum, and causes renal failure and death after approximately 10 weeks. According to the "Brenner hypothesis" [Brenner et al.; N Engl J Med 1982; 307: 652-9] intraluminal protein is reabsorbed by tubular epithelial cells which become thereby activated. Activated epithelial cells induce (1) inflammatory or (2) profibrotic second messenger pathways, or (3) undergo "epithelial-mesenchymal transition" (EMT) by themselves.

As mentioned above, Factor H is the key plasma/humoral regulator of the activated complement system. Factor H deficiency is known to cause renal diseases like aHUS or MPGN II. While Factor H deficiency induces/causes complement activation at the level of the endothelial cell surface or within the glomerular basement membrane, the supplementation of Factor H, which can at least in part pass the glomerular filter, will be able to decrease complement activation at the level of tubular epithelial cells and will thereby serve as therapeutic option for chronic/progressive renal disease caused by glomerular proteinuria.

The effect of Factor H administration can be tested by treating COL4α3 knock out mice with supraphysiological levels of Factor H purified from mouse serum, starting 4.5 weeks postpartum (earliest time point possible after weaning of the mice). Factor H is applied s.c., i.p. or i.m. Results in the treated group are compared to vehicle (NaCl 0.9%) treated controls. Mice are treated until they die (group 1), or are sacrificed after 7.5 and 9.5 weeks (group 2). Animals of group 2 are anesthetized, urine and blood samples are collected, kidneys are rapidly harvested, one kidney is formaldehyde fixed and used for immunohistology, and from the other kidney cortex is isolated for RNA extraction and subsequent real time reverse transcriptase PCR (RT-PCR) analysis.

The results show that in a mouse model of chronic glomerular proteinuria (1) chronic treatment with Factor H mitigates complement activation on the level of tubular epithelial cells, (2) reduces activation of inflammatory and profibrotic secondary pathways launched by tubular epithelial cells, (3) reduces degree of tubulointerstitial fibrosis, and (4) increases life span of COL4α3 knock out mice.

These results strongly support the use of Factor H for the treatment of chronic proteinuria, which is the final common key feature of chronic renal disease in general.

As already outlined proteinuria is not only indicating an acute or chronic defect of the function of the glomerular filter (e.g. nephritic or nephrotic syndrome) but also promotes progression of chronic renal disease via the induction of inflammatory and profibrotic processes in the tubular interstitium. Without exaggeration proteinuria can be seen as the final common pathway of chronic renal disease (CRD), and reduction of proteinuria or of the effects which are induced by proteinuria might proof of the key for efficient treatment of chronic renal disease.

Based on the concept that activation of the complement system on the apical surface of tubular epithelial cells is one of the major mediators in the pathogenic cascade of events in proteinuria caused CRD, treatment via Factor H (e.g. infusion of up to 80 ml FFP/kg body weight/treatment or i.v. or s.c. or i.m. administration of the Factor H equivalent of 80 ml FFP/kg body weight) is increasing plasma Factor H above physiological level (e.g. twofold) and is resulting in (a) the availability of Factor H on the apical surfaces of tubular epithelial cells which is then (b) decreasing activation of the complement system at this side.

In patients in whom disease is caused by a mutation of the Factor H gene which results in the expression of a protein with intact cell binding characteristics while being functionally defect (e.g. MPGN II based on a mutation of SCR 4 of Factor H: Licht et al, Kidney Int 2006) treatment via FFP (e.g. infusion of up to 80-120 ml FFP/kg/treatment or i.v. or s.c. or i.m. administration of the Factor H equivalent of 80-120 ml FFP/kg body weight) aiming at raising plasma Factor H levels up to two- or threefold is resulting in competitive binding of intact Factor H molecules to cell surfaces and subsequent reduction of complement activation.

Therapeutic success is indicated by (a) reduction in complement activation (increased C3, decreased C3b), (b) reduction (or at least prevention of further increase) of hematuria and proteinuria, and (c) stabilization —possibly improvement—of renal function.

The invention claimed is:

1. A method of treating dense deposit disease (DDD), comprising administering to a patient in need thereof purified functional Factor H concentrate in an amount that raises the patient's plasma levels of Factor H at least 10% above the level of the patient's endogenous Factor H.

2. The method of claim 1, wherein the patient has a Factor H defect resulting in the absence of Factor H from the patient's plasma.

3. The method of claim 1, wherein the patient has a Factor H defect that affects Factor H binding to membranes.

4. The method of claim 3, wherein the Factor H defect is a mutation in the recognition domain of Factor H.

5. The method of claim 1, wherein the patient has a Factor H defect that affects Factor H function while Factor H binding to membranes is unaffected.

6. The method of claim 5, wherein the Factor H defect is a mutation in the recognition domain of Factor H.

7. The method of claim 5, wherein the Factor H defect affects heparin binding.

8. The method of claim 1, wherein therapeutic success is indicated by an increase of C3 or a decrease of C3b.

9. The method of claim 1, wherein therapeutic success is indicated by an increase of C3 and a decrease of C3b.

10. The method of claim 1, wherein the Factor H is a recombinant Factor H.

11. The method of claim 1, wherein plasma levels of Factor H of at least 50% above the level of the patient's endogenous defective Factor H are achieved.

12. The method of claim 11, wherein plasma levels of Factor H at least 100% above the level of the patient's endogenous defective Factor H are achieved.

13. The method of claim 12, wherein plasma levels of Factor H at least 200% above the level of the patient's endogenous defective Factor H are achieved.

14. The method of claim 13, wherein plasma levels of Factor H at least 300% above the level of the patient's endogenous defective Factor H are achieved.

* * * * *